United States Patent
Herdt et al.

(10) Patent No.: US 8,562,796 B2
(45) Date of Patent: Oct. 22, 2013

(54) CONTROL SYSTEM AND METHOD OF USE FOR CONTROLLING CONCENTRATIONS OF ELECTROLYZED WATER IN CIP APPLICATIONS

(75) Inventors: Brandon Herdt, Hastings, MN (US); Robert Ryther, St. Paul, MN (US)

(73) Assignee: Ecolab USA Inc., Saint Paul, MN (US)

(*) Notice: Subject to any disclaimer, the term of this patent is extended or adjusted under 35 U.S.C. 154(b) by 519 days.

(21) Appl. No.: 12/826,922

(22) Filed: Jun. 30, 2010

(65) Prior Publication Data

US 2012/0000488 A1  Jan. 5, 2012

(51) Int. Cl.
  C25B 15/02 (2006.01)
  C25B 1/26 (2006.01)
  C02F 1/461 (2006.01)
  C23G 1/02 (2006.01)
  C23G 3/04 (2006.01)

(52) U.S. Cl.
  USPC ...... 204/228.6; 204/237; 210/739; 210/748.2

(58) Field of Classification Search
  None
  See application file for complete search history.

(56) References Cited

U.S. PATENT DOCUMENTS

| | | | |
|---|---|---|---|
| 4,322,215 A * | 3/1982 | Huber et al. | 205/778.5 |
| 4,767,511 A | 8/1988 | Aragon | |
| 4,935,065 A | 6/1990 | Bull | |
| 4,940,946 A | 7/1990 | Nazaryan | |
| 5,422,014 A | 6/1995 | Allen et al. | |
| 5,445,722 A | 8/1995 | Yamaguti et al. | |
| 5,676,760 A | 10/1997 | Aoki et al. | |
| 5,853,562 A | 12/1998 | Eki et al. | |
| 5,858,201 A | 1/1999 | Otsuka et al. | |
| 6,110,830 A * | 8/2000 | Skrovan et al. | 438/688 |
| 6,270,680 B1 * | 8/2001 | Silveri et al. | 210/746 |
| 6,357,454 B1 | 3/2002 | Yokota et al. | |
| 6,405,900 B1 | 6/2002 | Kown | |
| 6,524,475 B1 | 2/2003 | Herrington et al. | |
| 6,638,364 B2 | 10/2003 | Harkins et al. | |
| 6,716,335 B2 | 4/2004 | Takesako et al. | |
| 6,719,891 B2 | 4/2004 | Ruhr et al. | |
| 6,767,408 B2 | 7/2004 | Kenowski et al. | |
| 7,238,272 B2 | 7/2007 | Sano | |
| 7,303,660 B2 * | 12/2007 | Buckley et al. | 204/232 |
| 7,614,410 B2 | 11/2009 | Kenowski et al. | |
| 2002/0023847 A1 | 2/2002 | Natsume | |
| 2002/0032141 A1 | 3/2002 | Harkins | |

(Continued)

FOREIGN PATENT DOCUMENTS

EP  1238945 A1  9/2002
JP  10024294 A  1/1998

(Continued)

OTHER PUBLICATIONS

Ecolab USA Inc. et al., PCT/IB2011/052828, "Notification of Transmittal of the International Search Report and the Written Opinion of the International Searching Authority, or the Declaration" mailed Mar. 15, 2012, 12 pages.

*Primary Examiner* — Harry D Wilkins, III
(74) *Attorney, Agent, or Firm* — McKee, Voorhees & Sease, P.L.C.

(57) ABSTRACT

Control systems for use of electrolysis solutions for automated recirculating or single-pass cleaning systems, such as clean-in-place (CIP) applications are disclosed. Control systems and methods for using automated chlorine output solutions for various cleaning applications are measurable over broad pH ranges. The control systems generate consistent and predictable electrolytic solutions and include a measurement system that identifies chlorine oxyanion concentration across broad ranges of pH, overcoming the sensitivity of chlorine monitors to pH and permitting use of the control systems to control cleaning systems.

51 Claims, 5 Drawing Sheets

(56) References Cited

U.S. PATENT DOCUMENTS

| | | |
|---|---|---|
| 2004/0004007 A1 | 1/2004 | Orolin et al. |
| 2006/0020427 A1 | 1/2006 | Kahn et al. |
| 2006/0076248 A1 | 4/2006 | Kindred |
| 2006/0283789 A1 | 12/2006 | Kadlec et al. |
| 2006/0286676 A1 | 12/2006 | Van Camp et al. |
| 2007/0131541 A1 | 6/2007 | Miyashita |
| 2008/0008621 A1 | 1/2008 | Ikeda et al. |
| 2008/0047844 A1 | 2/2008 | Miyashita |
| 2008/0173574 A1 | 7/2008 | Silveri |

FOREIGN PATENT DOCUMENTS

| | | |
|---|---|---|
| JP | 2002-001341 A | 1/2002 |
| JP | 2002-005879 A | 1/2002 |
| JP | 2008074491 A | 4/2008 |
| JP | 7031980 A | 6/2010 |
| KR | 10-2005-0119250 A | 12/2005 |
| WO | 00/33757 A1 | 6/2000 |
| WO | 2009/055093 A1 | 4/2009 |
| WO | 2009/057034 A1 | 5/2009 |
| WO | 2010/037389 A1 | 4/2010 |

* cited by examiner

CONTROL SYSTEM AND METHOD OF USE FOR CONTROLLING CONCENTRATIONS OF ELECTROLYZED WATER IN CIP APPLICATIONS

FIELD OF THE INVENTION

The invention relates to use of electrolytic technology including electrolyzed water solutions for automated recirculating or single-pass cleaning systems, such as clean-in-place (CIP) applications. In particular, the invention provides a control system and methods for use in generating consistent and predictable electrolytic solutions with measurable chlorine content for use in cleaning systems. Control systems are disclosed for automated chlorine output and measurement over a broad range of pH for use in and control of cleaning systems such as CIP systems.

BACKGROUND OF THE INVENTION

Clean-in-place (CIP) techniques use the combination of chemistry and mechanical action to clean the inside of a system without requiring the time consuming and labor intensive disassembly and manual cleaning of a system. CIP cleaning regimens are adapted for removing soils from the internal components of tanks, lines, pumps and other process equipment. Methods and systems for CIP cleaning are frequently used, for example, to clean processing equipment with liquid product streams, such as those used in the food and beverage, pharmaceutical, textile and laundry industries. Further discussion of CIP operations can be found for example in U.S. Pat. Nos. 6,197,739, 6,953,507 and 6,991,685, the complete disclosures of which are herein incorporated by reference in their entirety.

CIP operations generally include the circulation of chemistries (e.g., detergents, antimicrobials and the like) for periodic cleaning of a system. Often CIP methods involve a first rinse, the application of cleaning solutions, a second rinse with portable water, followed by resumed operations. The process can also include any other contacting step in which a rinse, acidic or basic functional fluid, solvent or other cleaning component such as hot water, cold water, etc. can be contacted with the equipment at any step during the process. In addition, a final portable water rinse step may be skipped in order to prevent contamination of the equipment with bacteria following the cleaning and/or sanitizing steps. Prior to resuming normal processing, chemistry residues are removed from the system and/or any product contacted by the cleaning chemistry is discarded.

There is an increasing demand for development of suitable compositions for CIP applications, including chemistries useful for cleaning, sanitizing and disinfecting. Onsite production of cleaning chemistries is also under increasing demand. Onsite chemistry production can be achieved through electrolysis of water and electrolytes to produce alkaline detergent solutions of sodium hydroxide (NaOH), hypochlorite solutions or chlorine for use as detergent, bleach, surface sanitizers and other disinfectant purposes. The electrolysis of water and salt using this process is well established. A basic solution of sodium hydroxide (or "caustic" or "alkali") as well as an acidic solution of hypochlorous acid is formed. Depending upon the structure of an electrochemical cell, various effluents may be produced. For example, a cell divided by a membrane(s) produces both hypochlorous acid and sodium hydroxide. Alternatively, an electrochemical cell not divided by a membrane produces sodium hypochlorite (commonly referred to as bleach). Products obtained from electrolysis of water and salt solutions provide a source of chlorine-based detergent and disinfectant having numerous cleaning and sanitizing capabilities. These chlorine-containing oxidants are biocidal agents that are effective in killing bacteria, viruses, parasites, protozoa, molds, spores and other pathogens.

Use of electrolysis solutions for CIP applications generates high and variable concentrations of chlorine requiring chlorine measurement to maintain concentrations sufficient for cleaning and sanitizing without reaching levels that are corrosive to CIP systems. As a result, accurate chlorine measurements are necessary for electrolytic CIP solutions. However, commercially-available chlorine monitors are designed for detecting less concentrated chlorine levels, such as those associated with water treatment methods (from about 0.5 ppm to about 3 ppm). See e.g., U.S. Pat. No. 5,422,014, describing the pH limitations of chlorine monitors, the complete disclosure of which is herein incorporated by reference in its entirety. As a result, chlorine content achieved from electrolysis solutions, pH variability in water supply to an electrolytic solution and/or water used to dilute electrolysis solutions preclude chlorine measurement as required for use of electrolytic solution for CIP applications.

Accordingly, it is an objective of the claimed invention to develop control systems and methods for measurable automated chlorine output for automated recirculating or single-pass cleaning systems, such as CIP applications.

A further object of the invention is to develop systems and methods for use of electrolysis solutions based on having measured correct chlorine oxyanion concentration.

A further object of the invention includes systems and methods for hands-free automation of chlorine measurement over broad ranges of pH.

BRIEF SUMMARY OF THE INVENTION

The invention provides control systems that include a measurement system that identifies chlorine oxyanion concentration across broad ranges of pH, overcoming the sensitivity of chlorine monitors to pH and permitting use of the control systems and associated methods for electrolysis solutions in various cleaning applications, such as clean-in-place (CIP) applications. Automated methods for use of electrolysis solutions measured for chlorine oxyanion concentrations are provided for CIP and other cleaning applications.

In one embodiment of the invention, the control system for automated recirculating or single-pass cleaning applications uses solutions of electrolytically-generated chlorine oxyanions, including for example, hypochlorite, chlorite, chlorate and perchlorate anions, includes an electrolysis solution, wherein a first portion is in fluid communication with a chlorine sensor. In addition, a pH modifier is in fluid communication with the first portion of electrolysis solution to enable accurate measurement of chlorine oxyanion concentration from approximately 10 ppm to 1000 ppm, and an output into the cleaning application is provided. The control system is suitable for use in various cleaning applications, including for example, CIP cleaning or sanitizing applications for food or beverage processing equipment, textile or laundry processing equipment and surfaces including plates, glasses, silverware and other food preparation, handling and serving equipment in need of cleaning or sanitizing.

In another embodiment of the invention, the control system for use in an automated recirculating or single-pass cleaning system utilizing solutions of electrolytically-generated chlorine oxyanions is described. According to the embodiment, the control system includes an electrochemical cell for in situ production of an electrolysis solution, wherein a first portion of the electrolysis solution is in fluid communication with a chlorine sensor. In addition, a carbon dioxide source is in fluid communication with the portion of the electrolysis solution measured by the chlorine sensor, which modifies the pH of that portion of the electrolysis to enable accurate measurement of chlorine oxyanion concentration from approximately 10 ppm to 1000 ppm, and a system output delivers the electrolysis solution to the cleaning system.

According to a further embodiment of the invention, the portion of the electrolysis solution modified for measurement of chlorine oxyanion concentration can then be discarded or delivered back to the control system for further circulation. In addition, a chlorine sensor output can be used to control the system itself. For example, according to one embodiment feedback signal may adjust the electrolysis solution level or volume pumping through the system. In addition, the feedback signal may control the electrolysis solution itself. For example, according to another embodiment, the feedback signal may adjust the electrolysis solution concentration.

According to another embodiment of the invention, a control system for measuring chlorine oxyanion concentration of an electrolysis solution for use in an automated recirculating or single-pass cleaning system includes an electrolyzed solution concentrate source and a dilution water source used to produce an electrolysis solution, a chlorine sensor in fluid communication with a first portion of the electrolysis solution, a pH modifier capable of controlling the pH of the first portion of electrolysis solution between about 5.5-7.5 to ensure accurate measurement of the chlorine oxyanion concentration from approximately 10 ppm to 1000 ppm, and a feedback loop mechanism initiated based on the chlorine sensor measurement to adjust the chlorine oxyanion concentration in the electrolysis solution.

An additional embodiment includes a method for cleaning or sanitizing using electrolytically-generated chlorine oxyanions for an automated recirculating or single-pass cleaning system, including obtaining an electrolysis solution from a control system, and applying the electrolysis solution to a cleaning system in need of cleaning or sanitizing. A further embodiment according to the invention includes a method for antimicrobial treatment using electrolytically-generated chlorine oxyanions in an automated recirculating or single-pass cleaning system, including diluting an electrolysis concentrate in water to produce an electrolysis solution, wherein the chlorine oxyanion concentration is measured with a control system according to the invention, and applying the electrolysis solution to a cleaning system in need of antimicrobial treatment.

These and other embodiments of the invention are disclosed herein.

DETAILED DESCRIPTION OF THE PREFERRED EMBODIMENT

The embodiments of this invention are not limited to particular control systems and methods for use of electrolytically-generated chlorine oxyanions for cleaning applications, including clean-in-place (CIP) applications, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form. Numeric ranges recited within the specification are inclusive of the numbers defining the range and include each integer within the defined range.

Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like.

The term "chlorine," as used herein, refers to chlorine compounds and chlorine oxyanions that exist in an electrolytically-generated solution (i.e. electrolysis solution). According to the invention, chlorine oxyanions may include for example, hypochlorite, chlorite, chlorate and perchlorate anions. Chlorine is further understood to include the terms "free chlorine" wherein the total concentration of hypochlorous acid and hypochlorite ion are measured. A person of ordinary skill in the art will appreciate that different chlorine species predominate at differing pHs as a result of the reactivity of chlorine to pH.

The terms "clean-in-place" and "CIP," as used herein, refer to various of cleaning applications, including for example cleaning of any internal and/or external components of a system. CIP shall further be understood to include both recirculating and/or free-standing or single-pass cleaning methods according to the invention. System components often include pipelines, vessels, tanks, pumps and other process equipment in need of cleaning by circulation or spraying with a cleaning composition. System components are used in a variety of industrial applications, including for example, food and beverage, pharmaceutical, textile and laundry processing equipment. Use of such processing equipment in the food and beverage industry for the industrial manufacture of foods and beverages, for example, results in surfaces becoming contaminated with soils as a result of contact with food or beverage product and such product remaining on a surface. Soils may include carbohydrates, proteinaceous soils, hardness soils, food oil soils and/or other soils and residues which arise from the manufacture of both liquid and solid foodstuffs. CIP applications remove, clean, sanitize and/or disinfect treated surfaces and soils that are often hard to remove. Further explanation of processing equipment soils is described in U.S. Pat. No. 8,398,781, the complete disclosures of which is herein incorporated by reference in its entirety.

The terms "electrolysis solution," "electrolytically-generated chlorine oxyanions," "chlorine oxyanion-containing electrolysis solutions," "electrolysis concentrate," and the like, as used herein, refer to any source of an electrolysis solution with a chlorine oxyanion source. The output from an electrochemical cell may vary depending on the structure of the cell and components added to the system. However, chlorine-containing electrolysis solutions are understood to include the same chemistry, namely chlorine ($Cl_2$), chlorite ($ClO_2$), chlorate ($ClO_3$), hypochlorous acid (HOCl), hypochlorite ions (OCl—), perchlorate anions and sodium hypochlorite (NaOCl) (as may be referred to as "bleach" products are may be referred to as anolyte, ECA, EO water, MOS and the like). One skilled in the art shall appreciate that any electrolysis solution containing a chlorine species may be included in the scope of the invention for providing a control system for use of electrolytically-generated chlorine oxyanions for CIP applications.

The terms "feed water," "dilution water," and "water" as used herein, refer to any source of water that can be used with the methods and systems of the present invention. Water sources suitable for use in the present invention include a wide variety of both quality and pH, and include but are not limited to, city water, well water, water supplied by a municipal water system, water supplied by a private water system, and/or water directly from the system or well. Water can also include water from a used water reservoir, such as a recycle reservoir used for storage of recycled water, a storage tank, or any combination thereof. It is to be understood that regardless of the source of incoming water for systems and methods of the invention, the water sources may be further treated within a manufacturing plant. For example, lime may be added for mineral precipitation, carbon filtration may remove odoriferous contaminants, additional chlorine or chlorine dioxide may be used for disinfection or water may be purified through reverse osmosis taking on properties similar to distilled water. As a result of the variety of water sources and subsequent treatment regimes there is a wide variability in water quality feeding into a CIP system according to the invention.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

According to embodiments of the invention, control systems and methods for use of control systems with electrolysis solutions for automated recirculating or single-pass cleaning systems, such as CIP applications are provided. The systems and methods allow for the use of controlled chlorine solutions for various CIP applications and provides significant benefit in CIP applications by providing a controlled system for chlorine concentration across a broad range of pH in order to use electrolyzed water solutions for CIP applications. The systems and methods according to the invention are suitable for numerous CIP applications, including for example food and beverage manufacturing plants where various cleaning, disinfecting or sanitizing chemistries are customarily used. Rather than varying known parameters of CIP cleaning compositions, such as amount or concentration of detergent or cleaning compositions, the invention provides means for using electrolysis solutions without any additional chemical detergents for CIP cleaning.

According to the invention, systems are provided for generating automated levels of chlorine in an electrolysis solution. For use in cleaning applications, such as CIP applications, electrolysis solutions require consistent, accurate and reproducible concentrations of chlorine without the need for continuous adjustment of flow rates of the solution or other chemical additives. Chlorine-containing electrolysis solutions generally range between about 10-1000 ppm chlorine, preferably from about 10-200 ppm chlorine, with a pH range from about 5-11, wherein changes in chlorine significantly impacting the pH of an electrolysis solution. In addition, changes in pH of water fed into an electrolytic cell and/or used for dilution of an electrolysis solution, impact the pH of the solution and have a negative effect on the sensitivity and accuracy of chlorine sensors.

The control systems and methods according to the invention provide consistent, accurate and reproducible user-control of pH of both (a) a portion of electrolysis solution that is measured by a chlorine sensor and (b) chlorine oxyanion concentrations for use in a particular cleaning system, providing a significant benefit in enabling the use of chlorine oxyanion-containing electrolysis solutions for various cleaning applications. According to an embodiment of the invention, the final pH of a portion of electrolysis solution used for measuring chorine oxyanions with a chlorine probe or sensor for CIP applications is between about 5.5-7.5, preferably from about 5.5-7.0 and most preferably from about 5.5-6.5 and is maintained within a range of less than or equal to 0.75 pH units, more preferably within less than or equal to 0.5 pH units, and most preferably within less than or equal to 0.25 pH units of the desired pH range without requiring adjustment of the flow rate of either the electrolysis solution and/or a pH modifier. According to the invention, the stabilized pH range of a portion of electrolysis solution measured by the chlorine sensor eliminates chlorine sensor error and permits use of water supplied to an electrolytic cell and/or used to dilute an electrolysis solution having highly variable quality and pH.

In addition to control systems for maintaining controlled pH of a portion of electrolysis solution to enable the use of chlorine oxyanion probes, control systems described herein provide feedback of the chlorine oxyanion content to the control system for automated control over the system. The control system according to the invention further permits the control of the electrolysis solution chlorine oxyanion concentration by responding to the chlorine sensor concentration measurement.

Control Systems

Figure 1:
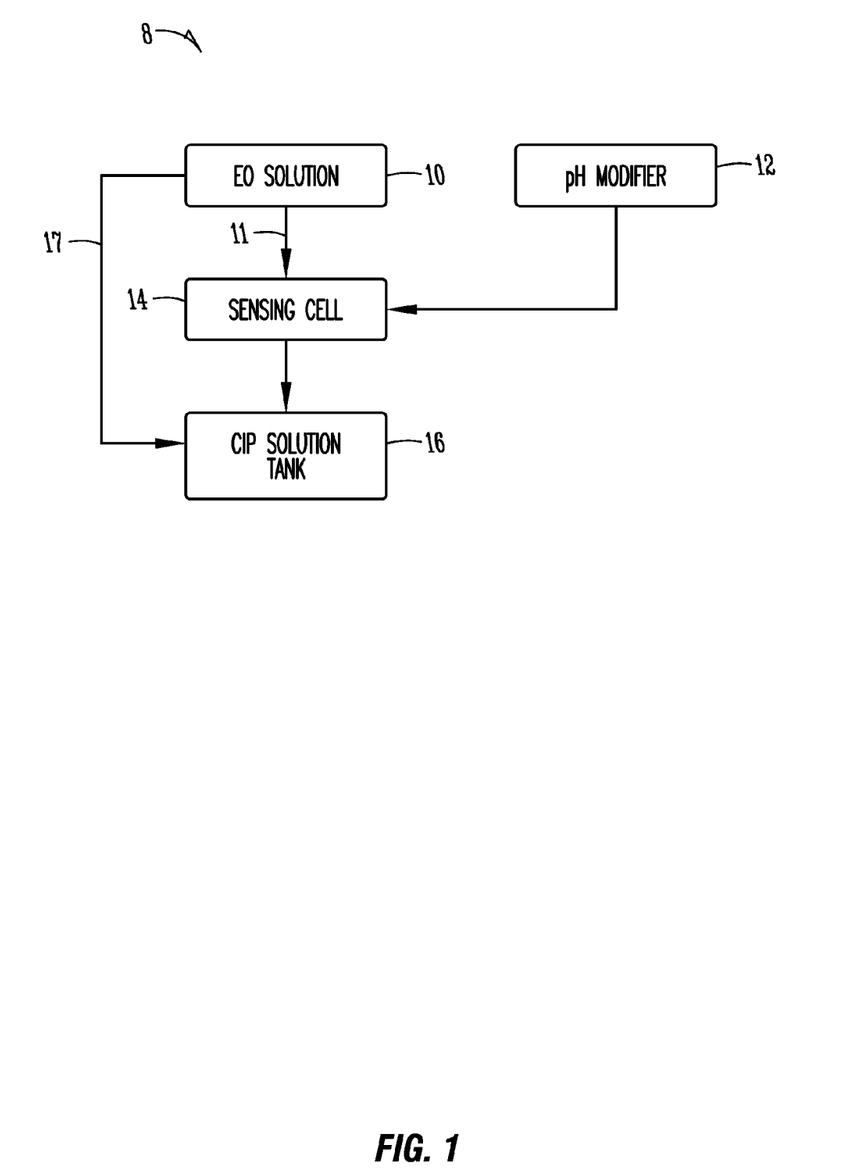
FIG. 1 shows a schematic diagram of an embodiment of the control system according to the invention used to obtain chlorine oxyanion concentration measurements from a portion of an electrolysis solution.
Figure 2:
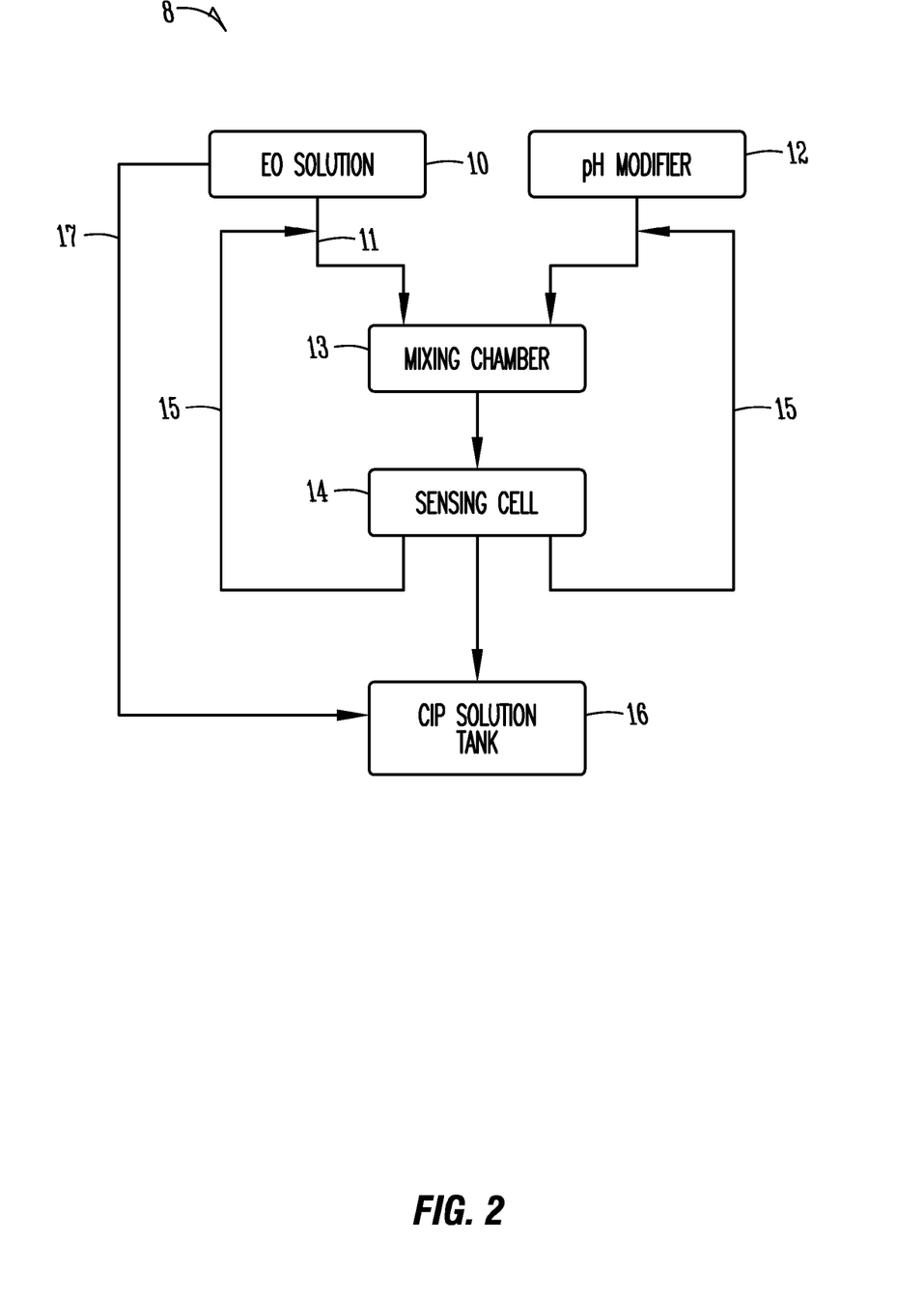
FIG. 2 shows a schematic diagram of an additional embodiment of the control system according to the invention used to obtain chlorine oxyanion concentration measurements from a portion of an electrolysis solution.

FIGS. 1 and 2 illustrate embodiments of the invention for use of a control system to obtain a chlorine oxyanion concentration measurement from a portion of an electrolysis solution. As described, an embodiment of the invention includes a chlorine oxyanion measurement system for automated control of a cleaning system using electrolysis solutions. As shown in FIG. 1, an embodiment of the invention includes a control system 8 comprising, consisting of or consisting essentially of an electrolysis solution (any electrolytically-generated chlorine oxyanions source) 10, a pH modifier 12, a sensing cell 14, a distribution system for providing fluid communication 11 between a first portion of the electrolysis solution, pH modifier and the sensing cell, and a distribution system 17 for providing fluid communication of a second portion of the electrolysis solution with the CIP solution tank 16. According to the invention, the second portion of the electrolysis system 17 does not require fluid communication with the pH modifier 12 and/or sensing cell 14 for chlorine oxyanion concentration measurement. The control system according to the invention provides pH adjustment for a first portion of the electrolysis solution providing accurate measurement of the chlorine oxyanion concentration from at least approximately 10 ppm to 1000 ppm.

FIG. 2 illustrates an additional schematic diagram of an embodiment of the present invention wherein a measurement of chlorine oxyanion concentration is obtained from a portion of an electrolysis solution. An embodiment of the invention includes a control system 8 for a user-controlled chlorine concentration for CIP applications that comprises, consists of or consists essentially of an electrolysis solution 10, a pH modifier 12, a mixing chamber 13, a sensing cell 14, a distribution system for providing fluid communication 11 between a first portion of the electrolysis solution and pH modifier to the sensing cell, and a distribution system for a second portion of electrolysis solution 17 provided to a CIP solution tank 16 according to the invention. The mixing chamber 13 provides an additional segment of liquid communication for mixing a pH modifier 12 with the electrolysis solution 10. For example, a mixing chamber 13 may be included to ensure adequate mixing an electrolytically-generated chlorine solution 10 with a pH modifier 12 according to the invention.

The control system 8 may optionally comprise, consist of or consist essentially of a feedback control mechanism for the system 15, such as a feedback loop depicted in FIG. 2. According to this optional embodiment of the control system, a pH probe is additionally housed within the sensing cell 14 and is used to determine the pH of the first portion of electrolysis solution 11 that is measured by the chlorine probe. The pH probe signal initiates a feedback mechanism for the pH modifier 12 (acid and/or alkaline modifiers described according to the invention) and/or electrolysis solution 10. The feedback mechanism 15 preferably adjusts the pH modifier 12 feed rate to the first portion of electrolysis solution 11 in order to adjust the pH and achieve the desired pH of the side stream of electrolysis solution. Once the side stream pH has attained the desired level as determined by the pH probe, the chlorine probe can then be used to measure the chlorine oxyanion concentration for use in the control of the system. According to a preferred embodiment of the invention, the control system achieves desired pH concentration ranges via a feedback loop mechanism 15 that adjusts the flow rates of the pH modifier 12 of the control system.

Figure 3:
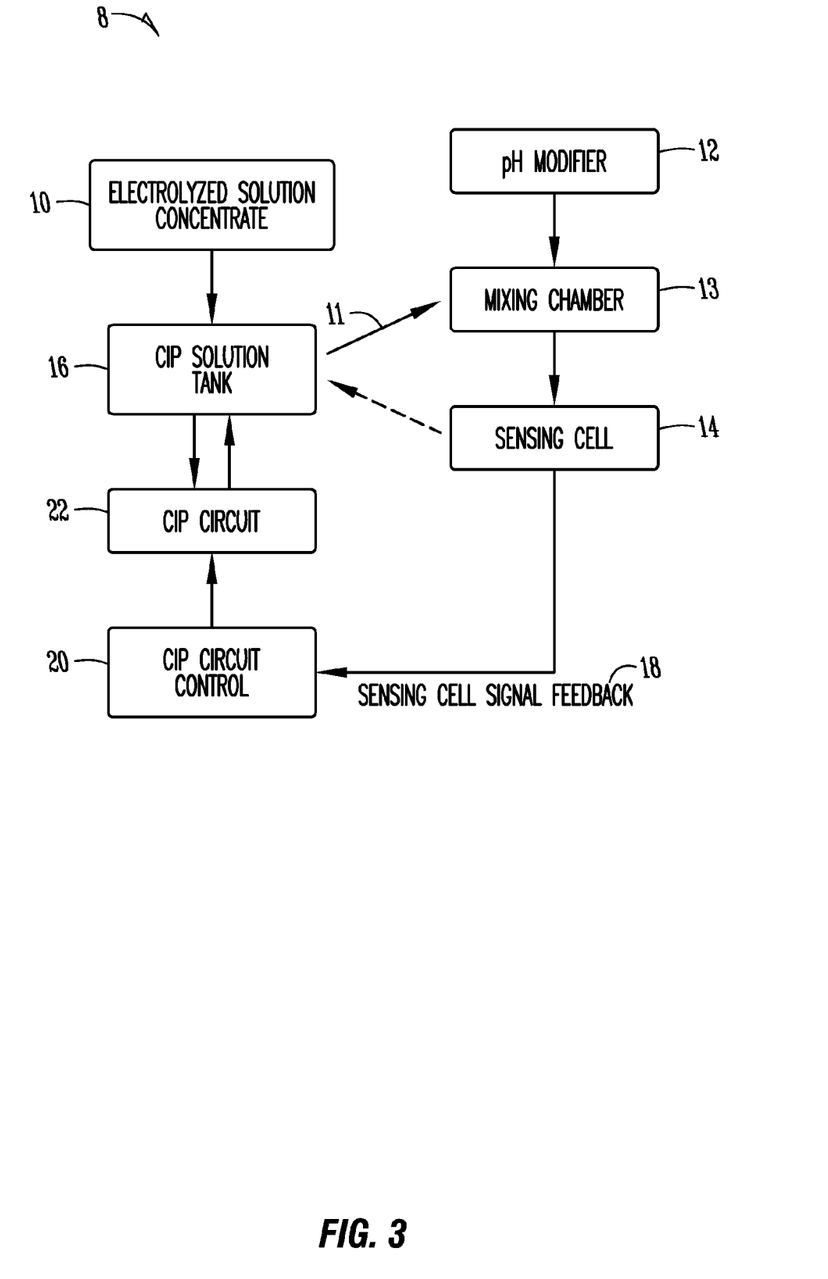
FIG. 3 shows a schematic diagram of an embodiment of the invention with a controlled CIP system as a result of effective chlorine oxyanion concentration measurement.
Figure 4:
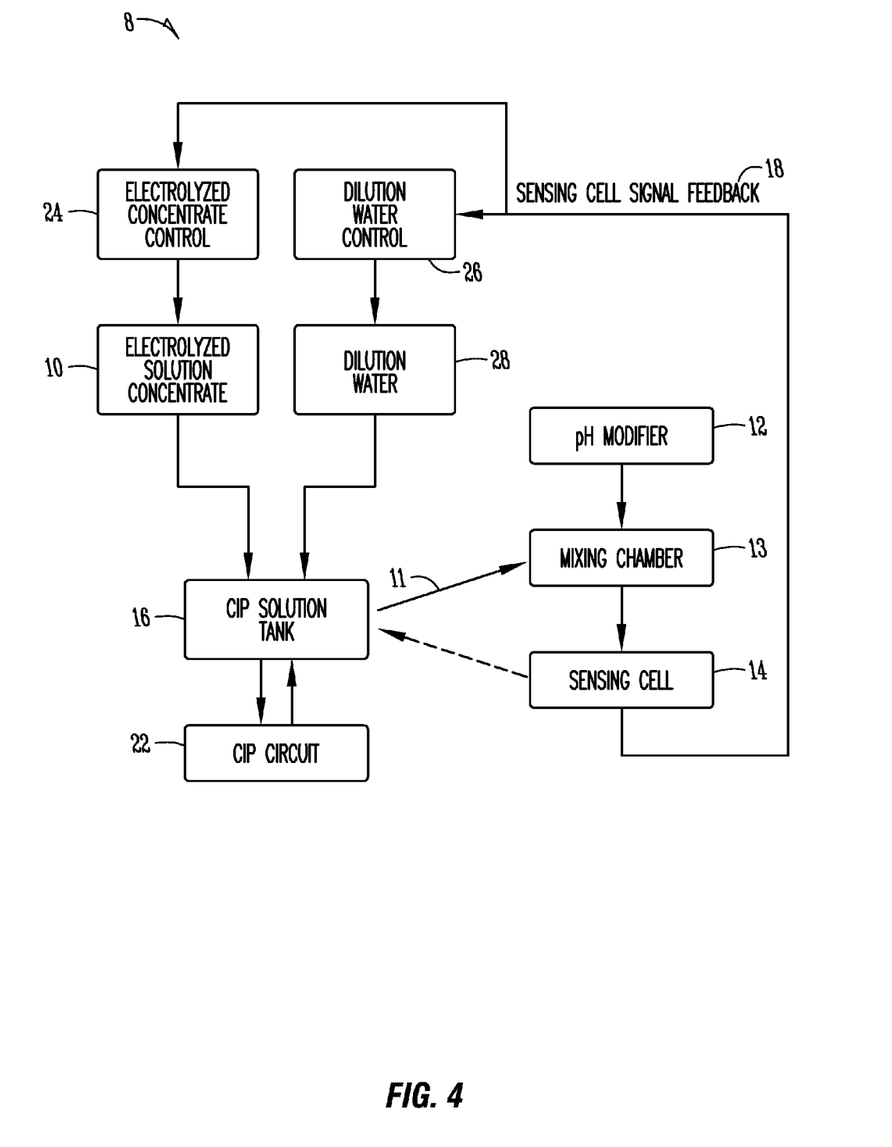
FIG. 4 shows an additional schematic diagram of a further embodiment of the invention with a controlled CIP system as a result of effective chlorine oxyanion concentration measurement.

FIGS. 3 and 4 show further embodiments of the invention wherein the cleaning system, such as a CIP system, is controlled as a result of having an effective chlorine oxyanion concentration measurement by the chlorine probe. According to further embodiments of the invention, the correct measurement of the chlorine oxyanion concentration (systems for which are disclosed in FIGS. 1 and 2) allow control of the CIP system itself, such as requesting performance of a desired CIP system change.

FIG. 3 shows a diagram of an embodiment of the control system 8 that comprises, consists of or consists essentially of an electrolysis solution concentrate 10, a distribution system for providing fluid communication 11 between a portion of the CIP solution tank 16 and the mixing chamber 13, a pH modifier 12, a sensing cell 14, and a sensing cell signal feedback 18 in communication with the sensing cell 14 and a CIP circuit control 20, wherein the CIP circuit control 20 is in communication with the CIP circuit 22. According to the embodiment of the invention, the control system provides feedback of the chlorine oxyanion content measured by the sensing cell 14 to the CIP circuit control 20 and CIP circuit 22 in order to provide mechanical-type controls of the cleaning system. As a result, the embodiment of the invention permits the CIP system to respond to the chlorine probe measurement. For example, a chlorine concentration measurement by the chlorine probe may initiate a recirculation mode of the CIP circuit control 20. Alternatively, the chlorine concentration measurement by the chlorine probe may initiate an ON/OFF mode for the CIP circuit control 20 once a targeted chlorine oxyanion concentration is achieved.

FIG. 4 shows an additional diagram of an embodiment of the invention, wherein the CIP system is further controlled as a result of having an effective chlorine oxyanion concentration measurement by the sensing cell 14. A control system 8 according to the invention as shown in FIG. 4 comprises, consists of or consists essentially of a CIP circuit 22, a distribution system for providing fluid communication 11 between a portion of the CIP solution tank 16 and the mixing chamber 13, a pH modifier 12, a sensing cell 14, and a sensing cell signal feedback 18 in communication with the sensing cell 14 and an electrolyzed concentrate control 24 and/or dilution water control 26, wherein the controls 24, 26 are in respective communication with an electrolyzed solution concentrate 10 and dilution water 28.

According to this embodiment of the invention, the feedback 18 is able to control the electrolyzed solution concentrate 10, dilution water 28 and/or an electrolytic cell (any of its input sources, such as brine or water) making the electrolyzed solution concentrate in order to respond to the chlorine oxyanion concentration measurement obtained from the chlorine sensor and adjust the chlorine oxyanion concentration output from the control system according to the invention. According to this embodiment of the control system, the electrolyzed concentrate control 24 communicates the need for addition of electrolyzed solution concentrate 10 to the CIP solution tank 16, and the dilution water control 26 communicates the need for addition of dilution water 28 to the CIP solution tank 16. As a result, the control system according to the invention provides feedback of the measured chlorine oxyanion concentration to the CIP system to permit the CIP system to respond to the chlorine probe measurement through a recirculation loop adjusting the amount of electrolyzed solution concentrate 10 and/or dilution water 28 provided to the CIP solution tank 16 in order to reach a desired chlorine oxyanion concentration.

The control system 8 according to the invention comprises a source of any electrolytically-generated chlorine oxyanions 10, namely a chlorine-containing electrolysis solution for providing one-step cleaning, sanitizing and antimicrobial effects for CIP applications. The electrolytically-generated chlorine oxyanion source may be any electrolysis solution and/or an electrolyzed solution concentrate. According to one embodiment of the invention an electrochemical cell produces the electrolysis solution and/or electrolyzed solution concentrate in situ. According to another embodiment, an electrolyzed solution concentrate is diluted with dilution water to form an electrolysis solution. According to an alternative embodiment, a side stream of electrolytically-generated chlorine is connected in fluid communication to the control system, wherein the target chlorine concentration is validated. According to a further embodiment, the validated chlorine concentration of a side stream of electrolytically-generated chlorine signals the addition of the chlorine solution and optionally additional water source into a CIP solution tank 16 for use in CIP applications according to the invention.

It is appreciated by the control systems according to the invention that the pH of an electrolysis solution 10 or electrolyzed solution concentrate 10 may initially be from about 5 to about 11 and the pH of the first portion of the electrolysis solution in fluid communication 11 with the sensing cell 14 is adjusted according to the control systems of the present invention to a range from about 5.5-7.5, preferably from about 5.5-7.0 and most preferably from about 5.5-6.5 to obtain an accurate chlorine oxyanion concentration measurement.

According to the invention, the electrolysis solution 10 provides a minimum concentration of chlorine oxyanions for antimicrobial efficacy, sanitizing and cleaning. An embodiment of the invention includes a chlorine source having from about 20 ppm to about 1000 ppm chlorine. According to another embodiment the source is an electrolysis solution having from about 10 ppm to about 200 ppm chlorine, preferably from about 30 ppm to about 200 ppm, more preferably from about 50 ppm to about 200 ppm chlorine. According to a preferred embodiment the electrolytically-generated chlorine oxyanions range from about 10 ppm to about 200 ppm and provides cleaning, sanitizing and antimicrobial efficacy without causing corrosion of CIP systems, which are typically comprised of stainless steel parts.

The control systems 8 according to the invention comprise, consist essentially of and/or consist of a chlorine sensor to measure chlorine oxyanion concentration of a first portion of the electrolysis solution housed within a sensing cell 14. The first portion of the electrolysis solution 11 flows through the sensing cell for chlorine concentration detection and measurement. As one skilled in the art will understand, the invention is not limited according to the type of chlorine sensor or monitor selected. For example, any amperometric monitor, colorimetric monitor, selective ion electrode monitor or polarographic membrane probe may be used according to the systems and methods of the invention to provide consistent control of chlorine and pH levels.

According to an optional embodiment of the invention, the sensing cell 14 comprising a chlorine sensor may additionally comprise a plurality of sensing elements, including for example a pH sensor. According to the embodiment of the invention wherein both a chlorine and pH sensor are housed within the sensing cell 14 of the control system 8, an electrolytically-generated chlorine solution 10 is passed through the sensing cell 14 wherein both a chlorine sensor and a pH sensor are housed and obtain measurements of the chlorine species and pH. Certain embodiments of the invention comprising a feedback mechanism to control the pH of the electrolysis solution for accurate measurement of chlorine concentration comprise a pH sensor.

According to further embodiment of the control system 8, the sensing cell 14, and any plurality of sensors or probes housed therein may be monitored by a user. For example, an embodiment of the invention includes a means of telecommunication for reporting process control parameters to a user in order to verify the electrolysis solution has achieved the targeted chlorine and/or pH concentrations.

According to a further embodiment of the invention, the distribution systems for providing fluid communication within the control system 8 may be any means of fluid communication or connection, including for example, a circulation system and/or a pump system. Any fluid communication or connection may further comprise an introduction tee for the addition of electrolysis solution 10, pH modifier 12 and/or dilution water 28. The distribution systems for providing fluid communication may further comprise at least one flow control valve for establishing an adjustable flow rate for the electrolysis solution 10, pH modifier 12 and/or dilution water 28.

The control systems 8 according to the invention comprise, consist essentially of and/or consist of a pH modifier 12 in fluid communication 11 with the first portion of the electrolysis solution within the sensing cell 14. Suitable pH modifiers according to the invention may include, for example, gaseous and/or liquid acidulants and alkaline buffering agents, including for example, carbon dioxide gas, sodium, calcium or potassium hydroxide, sodium or potassium carbonate or bicarbonate, and/or, mono-, di- or tri-protic mineral acids, such as hydrogen chloride. According to an embodiment, the pH modifier is an acidulant buffer introduced to the electrolysis solution to lower the pH to improve chlorine sensor sensitivity, due to the measurement errors obtained from chlorine measurement systems in water systems with pH above approximately 8. According to a preferred embodiment, an acidulant buffer may be added at an introduction tee within the fluid communication means 11 to adjust the pH of the first portion of the electrolysis solution being measured in the sensing cell 14. Preferably, carbon dioxide gas is added as an acidulant to buffer the first portion of the electrolysis solution at a fixed flow rate to provide pH adjustment of the solution into a suitable range for use of the chlorine sensor. As will be appreciated by a skilled artisan, use of buffers, such as carbon dioxide gas, adjust pH by forming carbonic acid when dissolved in solution to decrease solution pH to approximately 5-7, preferably from 5.5-6.5, based on the amount of carbon dioxide added to the first portion of the electrolysis solution.

According to a preferred embodiment, the flow rate of the carbon dioxide acidulating buffer is constant and does not require manual adjustments to maintain a targeted pH range of the first portion of the electrolysis solution in order to obtain accurate chlorine concentration measurements. The control system 8 maintains a desired pH range of the first portion of the electrolysis solution from about 5.5-7.0 and most preferably from about 5.5-6.5, within about 0.7 pH units, preferably within about 0.5 pH units and most preferably between about 0.3 pH units from the desired pH range. According to one embodiment of the invention a carbon dioxide flow rate of approximately 300 ml/min is established to maintain a pH range of the electrolysis solution from about 5.5 to 7.5 across the broad range of chlorine content within the first portion of the electrolysis solution, namely from about 10 ppm to about 200 ppm when the first portion of the electrolysis solution is also provided to the sensing cell at a constant feed rate.

Methods of Cleaning

According to an embodiment of the invention, methods for cleaning, sanitizing, disinfecting and antimicrobial efficacy in automated recirculating or single-pass cleaning applications, such as CIP applications are disclosed. As one skilled in the art would understand, methods of cleaning, sanitizing, disinfecting and antimicrobial efficacy are achieved based on the level of chlorine provided to a CIP system in need of treatment. According to a preferred embodiment, methods for a one-step cleaning and sanitizing process are achieved. According to a further preferred embodiment, methods for antimicrobial treatment are achieved.

Methods of cleaning, sanitizing, disinfecting and antimicrobial efficacy in a CIP application may be conducted according to known equipment use and configurations with the modifications described according to the invention to incorporate the control system of the present invention. An embodiment of the methods of use of electrolytically-generated chlorine oxyanions according to the invention, include contacting a cleaning an electrolysis solution obtained from a control system according to the invention with a surface in need of treatment. The electrolysis solution for use according to the methods of the invention has a desired chlorine concentration measurable across a broad pH range according to use of the control system of the invention.

Embodiments of the invention include use of the electrolysis solution for cleaning, sanitizing, disinfecting and antimicrobial efficacy for a variety of CIP applications, including for example food or beverage processing equipment, textile or laundry processing equipment or plates, glasses, silverware and other food preparation, handling and serving equipment. CIP applications according to the invention may include any recirculating or non-circulating cleaning systems.

According to a preferred embodiment, the electrolyzed water solution is put into contact with equipment in need of treatment by supply the solution through a means of fluid communication, such as an internal fluid circuit having a pump and return circuit system providing a recirculating system. According to an alternative embodiment, the electrolyzed water solution is put into contact with equipment in need of treatment by a spray device capable of washing the equipment and thereby providing a non-circulating system. According to a non-circulating embodiment, the spray device is used to wash a system, such as a vessel, which is then directed to a drain or to a pipeline directly leading to the drain wherein no re-circulation is established. The step of contacting an electrolyzed water solution with equipment may comprise introducing the solution with unheated, ambient temperature or heated water. Methods of cleaning may further include the step of rinsing the equipment.

Certain embodiments for methods of cleaning, sanitizing, disinfecting and administering antimicrobial effects to a CIP system may include applying or introducing the use solution into the system at a constant or variable flow rate. In addition, methods for cleaning a CIP system may be at temperatures ranging from incoming water temperature to above 70° C. Still further, methods for cleaning a CIP system may include contact times of at least about 10 seconds to about 120 seconds, preferably from at least 30 seconds.

As one of skill in the art will appreciate based on the disclosure of the present invention, the cleaning, sanitizing, disinfecting and antimicrobial treatment methods according to the invention may be further optimized according to variations in cleaning time, temperature, pressure, concentration of detergent or cleaning compositions, mechanics of operating a CIP cleaning application and the types of soil.

All publications and patent applications in this specification are indicative of the level of ordinary skill in the art to which this invention pertains. All publications and patent applications are herein incorporated by reference to the same extent as if each individual publication or patent application was specifically and individually indicated by reference.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

A Model Q45H/62 chlorine monitor (ATI, Analytical Technologies Inc., Collegeville, Pa.) was used as a chorine measurement system and combined according to the invention with a pH probe, flow system through the probe housing and a controller to convert electrical signal from the pH on $Cl_2$ probes into a measurable signal. The ATI meter has the capability to use the pH measurement to correct for variability in the sensitivity of the $Cl_2$ probe as a function of pH.

This system's potential to measure $Cl_2$ concentration with and without pH correction was analyzed. The pH probe was standardized prior to the test and the $Cl_2$ probe was standardized with a pH 7.0 solution triturated for $Cl_2$ concentration using the iodometric trituration method.

| Soln # | pH | Total Cl2 |
|---|---|---|
| 1 | 5.5 | 30 |
| 2 | 5.5 | 50 |
| 3 | 5.5 | 70 |
| 4 | 7 | 30 |
| 5 | 7 | 50 |
| 6 | 7 | 70 |
| 7 | 8.5 | 30 |
| 8 | 8.5 | 50 |
| 9 | 8.5 | 70 |

| Solution Run Order |
|---|
| 1 |
| 4 |
| 7 |
| 2 |
| 5 |
| 8 |
| 3 |
| 6 |
| 9 |
| 8 |
| 5 |
| 2 |
| 7 |
| 4 |
| 1 |
| 9 |
| 3 |
| 6 |

| Chlorine Titration | ATI Chlorine w/ pH Correction | ATI C12 no pH Correction | ATI pH |
|---|---|---|---|
| 30.5 | 35.2 | 40.05 | 5.22 |
| 30.5 | 30 | 33.1 | 6.55 |
| 30.5 | 29.6 | 7.7 | 7.95 |

-continued

| | | | |
|---|---|---|---|
| 51.3 | 63 | 70 | 5.21 |
| 51.3 | 50.5 | 56.2 | 6.35 |
| 51.3 | 50 | 12.8 | 7.94 |
| 71 | 82.8 | 44 | |
| 71 | 69 | 73.8 | 6.67 |
| 71 | 61.2 | 13.8 | 8.07 |
| 51.1 | 35.9 | 10.9 | 7.82 |
| 51.1 | 45.2 | 51.8 | 6.45 |
| 51.5 | 63.6 | 70.8 | 5 |
| 30.1 | 21.5 | 8.4 | 7.65 |
| 30.1 | 33.6 | 37.2 | 6.36 |
| 30.1 | 40 | 45.4 | 4.87 |

Example 2

Impact of adding electrolyzed water to 15 grain city water and 0 grain reverse osmosis water: The impact of adding EO solutions to water sources was measured to determine the pH of different water types as a function of concentration. Various volumes of EO solution were used to achieve available chlorine levels in the range used for both water treatment (0.5-3 ppm) and for the range expected for CIP applications (10-200 ppm). Chlorine concentration was measured using the iodometric titration method for measuring available chlorine in water solutions.

| ppm Av. Cl2 | City Water (15 gpg) | pH Delta |
|---|---|---|
| 0 | 7.79 | 0 |
| 0.195313 | 7.79 | 0 |
| 0.390625 | 7.8 | 0.01 |
| 0.78125 | 7.82 | 0.03 |
| 1.5625 | 7.84 | 0.05 |
| 3.125 | 7.85 | 0.06 |
| 6.25 | 7.87 | 0.08 |
| 12.5 | 7.91 | 0.12 |
| 25 | 7.99 | 0.2 |
| 50 | 8.11 | 0.32 |
| 100 | 8.23 | 0.44 |
| 200 | 8.43 | 0.64 |

| ppm Av. Cl2 | RO water | Delta pH |
|---|---|---|
| 0 | 6.13 | 0 |
| 0.195313 | 6.85 | 0.72 |
| 0.390625 | 7.23 | 1.1 |
| 0.78125 | 7.56 | 1.43 |
| 1.5625 | 7.96 | 1.83 |
| 3.125 | 8.28 | 2.15 |
| 6.25 | 8.53 | 2.4 |
| 12.5 | 8.76 | 2.63 |
| 25 | 8.93 | 2.8 |
| 50 | 9.09 | 2.96 |
| 100 | 9.22 | 3.09 |
| 200 | 9.28 | 3.15 |

The results demonstrate the impact of EO solutions on pH when added at levels above the range typically used for water treatment (0.5-3 ppm). As chlorine concentration increases (such as average chlorine content in EO solutions from approximately 10-200 ppm) the pH of the solution increases. The result is significant due to the sensitivity of chlorine sensors to change in pH due to the pKa of hypochlorous acid (chlorine). In addition, the impact of EO solutions is variable dependent upon the type of water (i.e. hard water versus reverse osmosis water). Use of reverse osmosis water source results in greater pH change compared to a hard water source with increasing amounts of chlorine.

Figure 5:
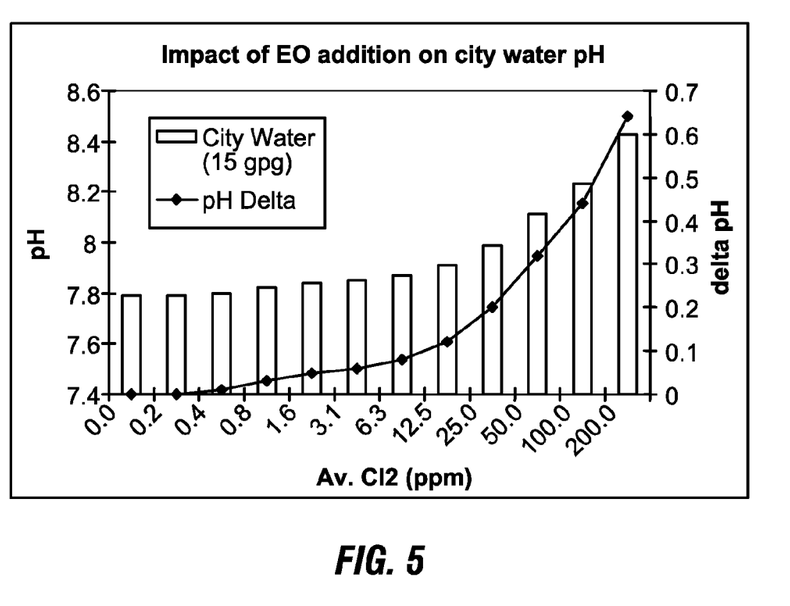
FIG. 5 shows the impact of electrolysis solution on the pH of a water source.
Figure 6:
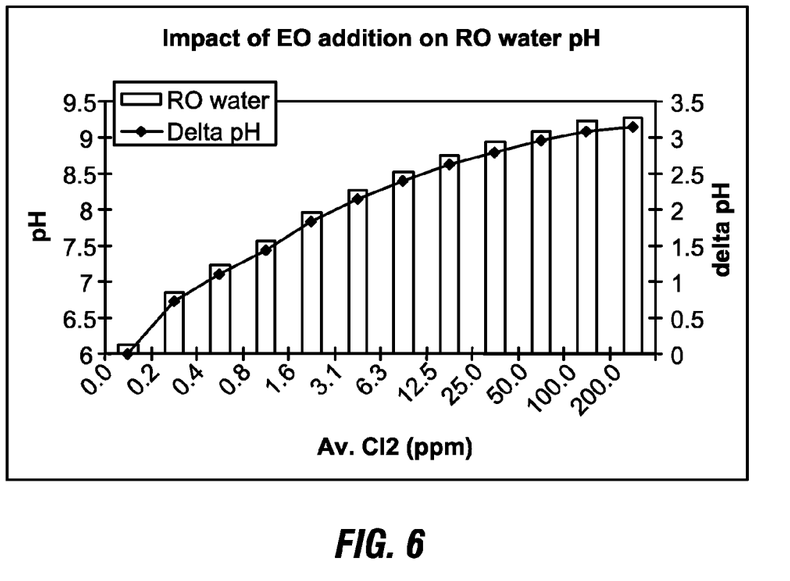
FIG. 6 shows the impact of electrolysis solution on the pH of a water source.

The demonstration of change in pH (non-compatible with use of chlorine sensors dependent upon constant pH ranges for sensing chlorine species) as a result of both the quality of water source and the dosage rate of EO solution with having varying chlorine content confirms the need for control systems according to the invention. FIGS. 5 and 6 demonstrate the dramatic increase in change of pH observed with the addition of chlorine in amounts equivalent to chlorine-containing EO solutions (i.e. 10-200 ppm) demonstrate the need for pH control for consistent and accurate chlorine detection in order to overcome the deficiencies of chlorine monitors.

Example 3

Impact of pH on a membrane covered polarographic sensor and controller: The response of a polarographic sensor was analyzed to determine the impact of pH on the response of a sensor to chlorine concentration. A Model Q45H/62 chlorine monitor (ATI, Analytical Technologies Inc., Collegeville, Pa.) was used to test varying pH ranges and determine the effect on the sensor's response.

A solution of water containing a fixed concentration of EO water (titrated for avg. $Cl_2$) was circulated through a flow through chamber containing the chlorine electrode for the ATI meter. The flow through chamber also contained a pH probe for monitoring the pH of test solutions along with the response of the probe to chlorine.

The chlorine probe was calibrated to a solution of EO at 50 ppm available chlorine and a pH of 7.0. The pH of the EO solution was adjusted up or down with 0.1M NaOH or 0.1M HCl respectively. The overall change in volume by addition of this solution was less than 1% ensuring any changes in response of the electrode were entirely based on the shift in pH. The experiment was run at three different concentrations ~30, 50 and 70 ppm average chlorine concentration. Chlorine concentrations were titrated at the beginning and end of the test using the iodometric method for measuring average chlorine in water.

| pH | Reading | error |
|---|---|---|
| 65.35 ppm Av. Cl2 start | | |
| 65.12 ppm Av. Cl2 end | | |
| 7.78 | 57.4 | −7.95 |
| 7.48 | 61.2 | −4.15 |
| 7.2 | 65.4 | 0.05 |
| 6.98 | 69.8 | 4.45 |
| 6.78 | 73.2 | 7.85 |
| 6.64 | 74.4 | 9.05 |
| 6.26 | 80.9 | 15.55 |
| 5.75 | 85.4 | 20.05 |
| 45.8 ppm Av. Cl2 start | | |
| 45.3 ppm Av. Cl2 end | | |
| 9.15 | 32.3 | −13.5 |
| 7.52 | 39.8 | −6 |
| 7.12 | 45 | −0.8 |
| 6.86 | 49.3 | 3.5 |
| 6.6 | 53.2 | 7.4 |
| 6.37 | 56.3 | 10.5 |
| 6.09 | 59.1 | 13.3 |
| 5.85 | 60.7 | 14.9 |
| 28.0 ppm Av. Cl2 start | | |
| 28.2 ppm Av. Cl2 end | | |
| 9.54 | 17.7 | −10.3 |
| 8.66 | 20.9 | −7.1 |
| 7.51 | 24.4 | −3.6 |
| 6.9 | 29.3 | 1.3 |

-continued

| 6.39 | 33.3 | 5.3 |
| 5.86 | 36.3 | 8.3 |

The results demonstrate there is significant error in commercially-available chlorine sensors as the pH of the EO solution shifts (up or down outside of a preferred range of about pH 5-7). Changes in pH can be based on the quality of water used for dilution of an EO solution and/or the amount of chlorine in a solution. The results further demonstrate the error in the chlorine sensor increases as average chlorine concentrations increase, illustrating the need for control systems according to the invention when chlorine concentrations from electrolytically-generated chlorine solutions are in the range of from about 10 ppm to about 200 ppm.

Example 4

Response of chlorine sensor to EO solutions at various pHs with and without the addition of $CO_2$: A stock solution of EO water was made up to a concentration of 40 ppm available chlorine from an EO concentrate produced by a MIOX Sal-80 generator fitted with an "Ox-cell" electrolytic cell. Chlorine concentration was measured using the iodometric method for measuring chlorine.

The 40 ppm EO solution had a native pH of 7.5 and was pumped through a chamber containing both a chlorine sensor and a pH probe (previously calibrated). The 40 ppm EO solution was introduced to the control system at a mixing tee at the rate of 600 ml/min. $CO_2$ gas was added as an acidulant to the mixing tee at a rate that caused the pH of the solution to drop to 6.10 relating to a $CO_2$ flow rate of approximately 300 ml/min. With the pH of the solution at 6.10 the chlorine probe was calibrated to output a signal that was measured as 40 ppm chlorine.

$CO_2$ was then turned off and the pH of the EO solution returned to pH 7.5. When $CO_2$ was turned back on the pH again dropped to 6.1 where the ppm chlorine indicated by the chlorine probe controller was measured. $CO_2$ was again turned off with the pH of the EO solution returning to 7.5. At this point a small amount of 5.0% NaOH was added to the EO solution to increase the pH to 8.35. This solution was pumped through the flow through cell and chlorine concentration and pH measured by the probes were recorded in the chamber. $CO_2$ was again turned on to inject $CO_2$ into the mixing tee. The flow control for the $CO_2$ was not changed from the rate required to bring the pH to 7.5 down to pH 6.1. When pH stabilized the chlorine sensor value and pH were recorded.

The test was repeated a third time with additional 5.0% NaOH solution added to the EO solution yielding a pH of 9.35. Again $CO_2$ was added to the mixing chamber without changing the flow rate. Concentration of chlorine as measured by the chlorine probe was recorded for both the native and $CO_2$ added pH conditions.

| Initial pH | Initial Cl2 reading (ppm) | pH with CO2 add | Cl2 reading w/CO2 add (ppm) |
| --- | --- | --- | --- |
| 7.5 | 21.5 | 6.1 | 41.2 |
| 8.35 | 7.1 | 6.06 | 40.4 |
| 9.35 | 2.4 | 6.26 | 40.5 |
| 9.95 | 1.0 | 6.21 | 39.8 |

As a final test the $CO_2$ value was opened so that its flow rate was approximately 1000 ml/min. with an 8.35 pH. Under these flow conditions the pH dropped to 5.5 and the measured chlorine value was 44.0 ppm.

The results demonstrate the ability of the control system of the present invention to provide a targeted electrolysis solution with a desired pH and chlorine content suitable for purposes of CIP applications. As demonstrated, the control system does not require a feedback loop or other means of adjustment. Rather, a hands-free means of control for providing a desired chlorine content in an electrolysis solution for CIP applications is provided according to the invention.

The inventions being thus described, it will be obvious that the same may be varied in many ways. Such variations are not to be regarded as a departure from the spirit and scope of the inventions and all such modifications are intended to be included within the scope of the following claims.

What is claimed is:

1. A control system for use with an automated recirculating or single-pass cleaning application that utilizes solutions of electrolytically-generated chlorine oxyanions comprising:
   (a) an electrolysis solution;
   (b) a first portion of said electrolysis solution connected in fluid communication with a chlorine sensor;
   (c) a pH modifier connected in fluid communication with said first portion of electrolysis solution to maintain a stabilized pH between about 5.5 to about 7.5 of said portion of electrolysis solution to enable accurate measurement of chlorine oxyanion concentration from approximately 10 ppm to 1000 ppm;
   (d) at least one flow control valve connected in fluid communication to said first portion of electrolysis solution to provide said pH modifier;
   (e) a feedback control loop connected in fluid communication to said flow control valve allowing recirculation or addition of electrolysis solution, water and/or pH modifier to said electrolysis solution to obtain a targeted chlorine oxyanion concentration from said system; and
   (f) an output into said cleaning application; wherein said system generates electrolysis solutions having controlled chlorine concentrations between approximately 10 ppm to 1000 ppm without requiring continuous adjustment of flow rates of said solutions or additional chemical additives as a result of said stabilized pH range of said first portion of electrolysis solution in fluid communication with said chlorine sensor; and wherein said first portion of electrolysis solution used for measurement of chlorine oxyanion concentration is discarded from said system or recirculated in said system.

2. The control system according to claim 1 wherein said electrolysis solution is used to clean or sanitize food or beverage processing equipment.

3. The control system according to claim 1 wherein said electrolysis solution is used to clean or sanitize textile or laundry processing equipment.

4. The control system according to claim 1 wherein said electrolysis solution is used for cleaning or sanitizing institutional plates, glasses, silverware or other food preparation and handling equipment.

5. The control system according to claim 1 wherein said electrolysis solution is any electrolytically-generated chlorine oxyanion source.

6. The control system according to claim 5 wherein said chlorine oxyanion concentration is from approximately 10 ppm to 200 ppm.

7. The control system according to claim 5 wherein said electrolysis solution has an initial pH from about 5 to about 11.

8. The control system according to claim 1 wherein said flow control valve connected in fluid communication to said first portion of electrolysis solution provides said pH modifier.

9. The control system according to claim 1 wherein said pH modifier is added to said first portion of electrolysis solution in communication with said chlorine sensor at a fixed rate to adjust the pH of said first portion of electrolysis solution to between about 5.5 to about 7.5.

10. The control system according to claim 9 therein said pH modifier is carbon dioxide gas.

11. The control system according to claim 9 wherein said pH modifier is an alkaline pH buffer solution.

12. The control system according to claim 9 wherein said pH modifier is an acid pH buffer solution.

13. The control system according to claim 9 wherein said pH modifier is a pH neutral buffer solution.

14. The control system according to claim 9 wherein said control system maintains the pH of said first portion of electrolysis solution within said pH range within less than or equal to 0.75 pH units without adjustment of a flow rate of said pH modifier or electrolysis solution.

15. The control system according to claim 9 wherein said control system maintains the pH of said first portion of electrolysis solution within said pH range within less than or equal to 0.5 pH units without adjustment of a flow rate of said pH modifier or electrolysis solution.

16. The control system according to claim 9 wherein said control system maintains the pH of said first portion of electrolysis solution within said pH range within less than or equal to 0.25 pH units without adjustment of a flow rate of said pH modifier or electrolysis solution.

17. The control system according to claim 1 further comprising an electrochemical cell capable of generating said electrolysis solution.

18. The control system according to claim 1 further comprising a pH probe connected in fluid communication with said first portion of electrolysis solution and said chlorine sensor.

19. The control system according to claim 1 wherein said feedback control loop adds further electrolysis solution to the system to achieve a targeted set point.

20. The control system according to claim 1, wherein said feedback control loop adds further pH modifier to the first portion of electrolysis solution to achieve a pH between about 5.5 and 6.5.

21. A method for cleaning or sanitizing using electrolytically-generated chlorine oxyanions for an automated recirculating or single-pass cleaning system, comprising:
(a) obtaining an electrolysis solution from the control system according to claim 1, and
(b) applying said electrolysis solution to said cleaning system.

22. The CIP cleaning or sanitizing method according to claim 21 further comprising generating an electrolysis solution on-site for use as said electrolysis solution.

23. The CIP cleaning or sanitizing method according to claim 21 wherein said electrolysis solution is any electrolytically-generated chlorine oxyanion source.

24. The CIP cleaning or sanitizing method according to claim 21 further comprising diluting said electrolysis solution with a water source.

25. The CIP cleaning or sanitizing method according to claim 21 further comprising rinsing said cleaning system after contact with said electrolysis solution.

26. A method for antimicrobial treatment using electrolytically-generated chlorine oxyanions in an automated recirculating or single-pass cleaning system, comprising:
(a) diluting an electrolysis concentrate in water to produce an electrolysis solution, wherein the concentration of chlorine oxyanions in said electrolysis solution is measured with the control system of claim 1; and
(b) applying said electrolysis solution to said cleaning system in need of antimicrobial treatment.

27. The method of antimicrobial treatment according to claim 26 wherein the electrolysis solution has a pH range in the range of about from 5 to about 11.

28. The method of antimicrobial treatment according to claim 26 wherein said control system maintains the pH of a measured portion of said electrolysis solution within said pH range within less than or equal to 0.75 pH units without adjustment of a flow rate of said pH modifier or electrolysis solution.

29. The method of antimicrobial treatment according to claim 26 wherein said control system maintains the pH of a measured portion of said electrolysis solution within said pH range within less than or equal to 0.5 pH units without adjustment of a flow rate of said pH modifier or electrolysis solution.

30. The method of antimicrobial treatment according to claim 26 wherein said control system maintains the pH of a measured portion of said electrolysis solution within said pH range within less than or equal to 0.25 pH units without adjustment of a flow rate of said pH modifier or electrolysis solution.

31. The method of antimicrobial treatment according to claim 26 wherein said pH modifier is provided at a fixed rate to adjust the pH of said measured portion of electrolysis solution.

32. The method of antimicrobial treatment according to claim 31 wherein said pH modifier is a source of carbon dioxide gas.

33. The method of antimicrobial treatment according to claim 26 further comprising a pH probe connected in fluid communication with said measured portion of electrolysis solution and said chlorine sensor.

34. The method of antimicrobial treatment according to claim 26 further comprising a feedback control loop mechanism connected in fluid communication with a flow control valve allowing recirculation or addition of electrolysis solution to obtain a targeted chlorine oxyanion concentration for use in said cleaning system.

35. The method of antimicrobial treatment according to claim 26 further comprising a feedback control loop mechanism connected in communication with a circuit control wherein said circuit control is triggered by said chlorine oxyanion concentration.

36. The method of antimicrobial treatment method according to claim 26 further comprising generating an electrolysis solution in situ from an electrolytic cell.

37. The method of antimicrobial treatment method according to claim 26 wherein said cleaning system is selected from the group consisting of a food or beverage processing equipment, textile or laundry processing equipment, a plurality of plates, glasses, silverware and other food preparation, handling or serving equipment, and combinations thereof.

38. A control system for use in an automated recirculating or single-pass cleaning system that utilizes solutions of electrolytically-generated chlorine oxyanions, comprising:

(a) an electrochemical cell for in situ production of an electrolysis solution, wherein a first portion of said electrolysis solution is in fluid communication with a chlorine sensor;
(b) a carbon dioxide source in fluid communication with said first portion of electrolysis solution for pH modification of said first portion of electrolysis solution to maintain a stabilized pH between about 5.5 to about 7.5 of said first portion of electrolysis solution to enable accurate measurement of chlorine oxyanion concentration from approximately 10 ppm to 1000 pm;
(c) at least one flow control valve connected in fluid communication to said first portion of electrolysis solution to provide said carbon dioxide source for said pH modification;
(d) a feedback control loop connected in fluid communication to said flow control valve allowing addition of further electrolysis solution, water and/or carbon dioxide to said electrolysis solution of said system to obtain a targeted chlorine oxyanion concentration from said system, wherein said system generates said electrolysis solution having controlled chlorine concentrations between approximately 10 ppm to 1000 ppm without requiring continuous adjustment of flow rates of said solutions or additional chemical additives a result of said stabilized pH range of said first portion of electrolysis solution in fluid communication with said chlorine sensor; and
(e) a system output for delivering electrolysis solution to said cleaning system;
wherein said first portion of electrolysis solution used for measurement of chlorine oxyanion concentration is discarded from said system.

39. The control system according to claim 38 wherein said system output delivers electrolysis solution for cleaning or sanitizing food or beverage processing equipment.

40. The control system according to claim 38 wherein said system output delivers electrolysis solution for cleaning or sanitizing institutional plates, glasses, silverware or other food preparation, handling and serving equipment.

41. The control system according to claim 38 wherein said system output delivers electrolysis solution for cleaning or sanitizing textile or laundry processing equipment.

42. The control system according to claim 38 wherein said electrolysis solution has a chlorine content from approximately 10 ppm to about 200 ppm.

43. The control system according to claim 38 wherein said electrolysis solution has an initial pH from about 5 to about 11.

44. The control system according to claim 38 wherein said first portion of electrolysis solution is adjusted to a pH from about 5.5 to about 6.5.

45. The control system according to claim 44 wherein said control system maintains the pH of said first portion of electrolysis solution within said pH range within less than or equal to 0.75 pH units without adjustment of a flow rate of said carbon dioxide or electrolysis solution.

46. The control system according to claim 44 wherein said control system maintains the pH of said first portion of electrolysis solution within said pH range within less than or equal to 0.5 pH units without adjustment of a flow rate of said carbon dioxide or electrolysis solution.

47. The control system according to claim 44 wherein said control system maintains the pH of said first portion of electrolysis solution within said pH range within less than or equal to 0.25 pH units without adjustment of a flow rate of said carbon dioxide or electrolysis solution.

48. The control system according to claim 38 wherein said carbon dioxide is provided at a fixed rate to adjust the pH of said first portion of electrolysis solution to between about 5.5 to about 7.5.

49. The control system according to claim 38 further comprising a pH probe connected in fluid communication with said first portion of electrolysis solution and said chlorine sensor.

50. The control system according to claim 38 wherein said feedback control loop adds further electrolysis solution to the system to achieve a targeted sot point of said chlorine oxyanion concentration.

51. The control system according to claim 50 where the flow control value can be operated to achieve a target concentration of said chlorine oxyanion species between about 10 ppm to about 200 ppm in the electrolysis solution used in said cleaning system.

* * * * *

UNITED STATES PATENT AND TRADEMARK OFFICE
CERTIFICATE OF CORRECTION

PATENT NO. : 8,562,796 B2  
APPLICATION NO. : 12/826922  
DATED : October 22, 2013  
INVENTOR(S) : Herdt Page 1 of 1

It is certified that error appears in the above-identified patent and that said Letters Patent is hereby corrected as shown below:

In the Claims

Col. 19, Claim 38, Line 25:
ADD after additives --as--

Col. 20, Claim 50, Line 35:
DELETE after targeted "sot"
ADD after targeted --set--

Signed and Sealed this
Seventeenth Day of December, 2013

Margaret A. Focarino
*Commissioner for Patents of the United States Patent and Trademark Office*